US012728204B2

(12) United States Patent
Holmqvist et al.

(10) Patent No.: US 12,728,204 B2
(45) Date of Patent: Sep. 8, 2026

(54) AUTO-INJECTION DEVICE

(71) Applicant: SHL MEDICAL AG, Zug (CH)

(72) Inventors: Anders Holmqvist, Varmdo (SE); Hsueh-Yi Chen, New Taipei City (TW)

(73) Assignee: SHL Medical AG, Zug (CH)

(*) Notice: Subject to any disclaimer, the term of this patent is extended or adjusted under 35 U.S.C. 154(b) by 0 days.

(21) Appl. No.: 18/363,564

(22) Filed: Aug. 1, 2023

(65) Prior Publication Data

US 2023/0372617 A1 Nov. 23, 2023

Related U.S. Application Data

(63) Continuation of application No. 18/354,865, filed on Jul. 19, 2023, which is a continuation of application No. 16/871,897, filed on May 11, 2020, now abandoned, which is a continuation of application No. 16/045,820, filed on Jul. 26, 2018, now Pat. No. 11,027,067, which is a continuation of application No. 15/809,398, filed on Nov. 10, 2017, now Pat. No. 12,109,397, which is a continuation of application No. 15/065,670, filed on Mar. 9, 2016, now Pat. No. 10,137,248, which is a continuation of application No. 14/365,635, filed as application No. PCT/SE2012/051365 on Dec. 10, 2012, now Pat. No. 9,867,940.

(60) Provisional application No. 61/570,921, filed on Dec. 15, 2011.

(30) Foreign Application Priority Data

Dec. 15, 2011 (SE) .................................. 1151197-9

(51) Int. Cl.

| | |
|---|---|
| ***A61M 5/20*** | (2006.01) |
| ***A61M 5/24*** | (2006.01) |
| ***A61M 5/31*** | (2006.01) |
| ***A61M 5/32*** | (2006.01) |

(52) U.S. Cl.

CPC ................ *A61M 5/20* (2013.01); *A61M 5/24* (2013.01); *A61M 5/31* (2013.01); *A61M 5/3202* (2013.01); *A61M 5/2033* (2013.01); *A61M 2005/206* (2013.01); *A61M 2005/2407* (2013.01); *A61M 2005/244* (2013.01); *A61M 2207/00* (2013.01); *A61M 2209/00* (2013.01); *Y10T 29/49826* (2015.01)

(58) Field of Classification Search

CPC ........ A61M 2005/206; A61M 2207/00; A61M 2209/00; A61M 5/20; A61M 5/2033; A61M 5/24; A61M 5/31; A61M 2005/2407; A61M 2005/244

See application file for complete search history.

(56) References Cited

U.S. PATENT DOCUMENTS

| | | | |
|---|---|---|---|
| 11,400,222 B2 * | 8/2022 | Hourmand ............. | A61M 5/31 |
| 2022/0054757 A1 * | 2/2022 | Hourmand ............. | A61M 5/24 |

* cited by examiner

*Primary Examiner* — William R Carpenter
(74) *Attorney, Agent, or Firm* — Perkins Coie LLP

(57) ABSTRACT

The present invention relates to an autoinjector device (10) for use in combination with a syringe (30), said syringe comprising a movable plunger; a needle; and a tubular needle shield (34). The claimed autoinjector device (10) comprises: an elongated housing having a proximal (11) and a distal end (12); a drive mechanism; a syringe holder (40) in order to support the fragile syringe and to prevent damage to the syringe. The invention furthermore relates to a method for assembly of the autoinjector device according to the invention.

20 Claims, 5 Drawing Sheets

30
30
12
40
10
40
48
58
15
16
16
11
A

AUTO-INJECTION DEVICE

FIELD OF THE INVENTION

The present invention relates to an auto injection device for use in combination with a syringe, and a method for assembling said syringe in the autoinjector device.

BACKGROUND OF THE INVENTION

Different types of autoinjectors are frequently used in order to facilitate administration of drugs to patients. When the proximal end of the autoinjector is correctly positioned against the intended area of the skin of the patient, an activation means on the autoinjector is pressed in order to activate the autoinjector. When activated, a needle rapidly punctuates the skin and the drug is delivered via the needle automatically.

There are two different categories of the autoinjectors on the market today. The first one uses custom designed medicament chambers, examples of these are described in WO2003/099358 and WO01/93926, while the second category uses standard pre-filled syringes. There are several advantages directed to the use of standard pre-filled syringes, for example the syringes have already been tested and approved in accordance with present regulations, which saves time and reduces the overall costs for the autoinjector. The present invention is directed to disposable autoinjectors used in combination with standard pre-filled syringes.

Since the autoinjectors are often used for self-administration of a drug to, the punctuation of the patients skin and the delivery of the drug via the needle are preferably performed rapidly which requires that a significant force is applied to the syringe by the drive mechanism. However, syringes are fragile and when the force of the drive mechanism is applied, there is a significant risk that the fragile syringe breaks.

In WO2007/083115 an autoinjector comprising a syringe support device intended to be arranged around the syringe and support the syringe at its front is disclosed. The support device reduces the risk of damage to the syringe but there is till a significant risk that the fragile syringe is damaged when a large force from the drive mechanism is applied upon activation of the autoinjector.

There is consequently still a need for an improved autoinjector device that further reduces the risk of damage to the syringe.

SUMMARY OF THE INVENTION

The present invention, defined in the appended claims, provides an autoinjector device that fulfils the needs defined above.

The autoinjector device of the present invention is elongated along a longitudinal axis A and has a proximal end and an opposing distal end and comprises

- a syringe having a substantially circular cross section having an outer diameter, said syringe having a proximal end comprising a neck and a distal end provided with a from the outer periphery of the container radially extending flange; said syringe further comprising a movable plunger, a needle and a tubular needle shield having a outer diameter which is larger than the outer diameter of the syringe,
- an elongated autoinjector housing comprising a space for said syringe;
- a driving mechanism arranged in the distal end of the housing in order to, when the autoinjector is activated, apply a force on the movable plunger;
- a syringe holder having a syringe holder wall with a substantially tubular shape, said holder wall having:
- an open distal end provided with a distal supporting collar arranged around the outer periphery of said syringe holder wall to support said syringe by the radially extending flange,
- an open proximal end provided with a proximal supporting collar arranged around the inner periphery of said syringe holder wall to support said syringe neck, and
- a slot extending from said open proximal end in the distal direction resulting in a C-shaped cross sectional shape of the syringe holder wall in the proximal end.

According to one aspect of the invention, the holder wall has a longitudinal length between the proximal supporting collar and the a distal supporting collar corresponding to the length of the syringe such that the a distal supporting collar of said syringe holder wall supports said radially extending flange of said syringe and said proximal supporting collar supports said neck of said syringe simultaneously when a force is applied on the movable plunger.

According to a further aspect of the invention, the proximal supporting collar has a inner diameter which is lesser than the outer diameter of the syringe.

According to another aspect of the invention, the proximal supporting collar has a inner diameter which is lesser than the outer diameter of the tubular needle covering shield.

According to a further aspect of the invention the proximal supporting collar is capable of flexing radially outward for allowing the tubular needle shield to pass through when the syringe is longitudinally mounted in relation to the longitudinal axis (A) within the syringe holder.

The claimed invention fulfils the needs defined above since the syringe holder according to the invention provides support for the syringe along the entire length of the syringe. Furthermore the distal end of the syringe holder, due to the corresponding length of the syringe holder, will be in contact with the radially extending flange at the distal end of the syringe and support the flange when the force from the drive mechanism is applied. Since the syringe is supported both at the proximal end by the collar in contact with the neck and at the distal end by the flat surface in contact with the flange of the syringe, the risk that the syringe is damaged when a drive force is applied by the drive mechanism is reduced considerably.

A further advantage with the claimed injector device is that the C-shaped proximal end of the syringe holder facilitates the fitting of the syringe in the holder since the C-shaped cross section makes it possible for the proximal end of the syringe holder to flex and thereby allow the tubular needle shield, even though it has a diameter exceeding the inner diameter of the collar, to be moved past the collar. Once the syringe is fitted in the syringe holder the C-shaped collar will provide the desired support around almost the entire syringe neck which is favourable since the load on the syringe neck will be distributed over a larger area and the risk of damage to the syringe is reduced considerably.

In one embodiment of the invention, the autoinjector device comprises guiding means to control the movement of the syringe holder within the autoinjector housing when the syringe holder is longitudinally mounted in relation to the longitudinal axis (A) within the autoinjector housing. This is a favourable embodiment of the autoinjector device since the guiding means will assist during the preparation of the autoinjector device. The syringe is first fitted in the syringe holder by introduction of the proximal end of the syringe into the syringe holder via the distal end of the syringe holder and then moved in the proximal direction of the autoinjector device to the intended position within the proximal housing section during assistance by the guiding means that facilitates the mounting of the syringe and the syringe holder in the housing.

In one embodiment of the invention, the guiding means comprises protrusions arranged along the outer periphery of the syringe holder wall and corresponding grooves arranged along the inner periphery of the autoinjector housing. This embodiment of the guiding means provides satisfying guiding during the preparation of the autoinjector device.

One embodiment of the invention comprises corresponding openings or windows in the autoinjector housing and the syringe holder which make it possible to easily verify that the syringe is correctly fitted in relation to the syringe holder and the antoinjector housing.

In one embodiment of the invention, the syringe holder comprises locking means that secures the syringe holder in relation to the autoinjector housing when the syringe holder is longitudinally mounted in relation to the longitudinal axis (A) within the autoinjector housing.

In one embodiment of the invention, the outer periphery of the proximal end of the syringe holder is radially supported by a contact surface on the inside surface of the autoinjector housing when the syringe holder is in a proximal position within the autoinjector housing. This embodiment is favourable since the contact surface of the autoinjector housing will prevent the proximal end of the syringe holder wall from flexing radially outwards, which ensures that the syringe remains in the intended position in the syringe holder when the drive force is applied by the drive mechanism.

The different embodiments described above could of course be combined and modified in different ways without departing from the scope of the invention that is defined by the claims. Further details of the invention will be described in the detailed description.

BRIEF DESCRIPTION OF THE DRAWINGS

One embodiment of the present invention is illustrated in the appended figures, said figures disclosing.

DETAILED DESCRIPTION

Figure 3A:
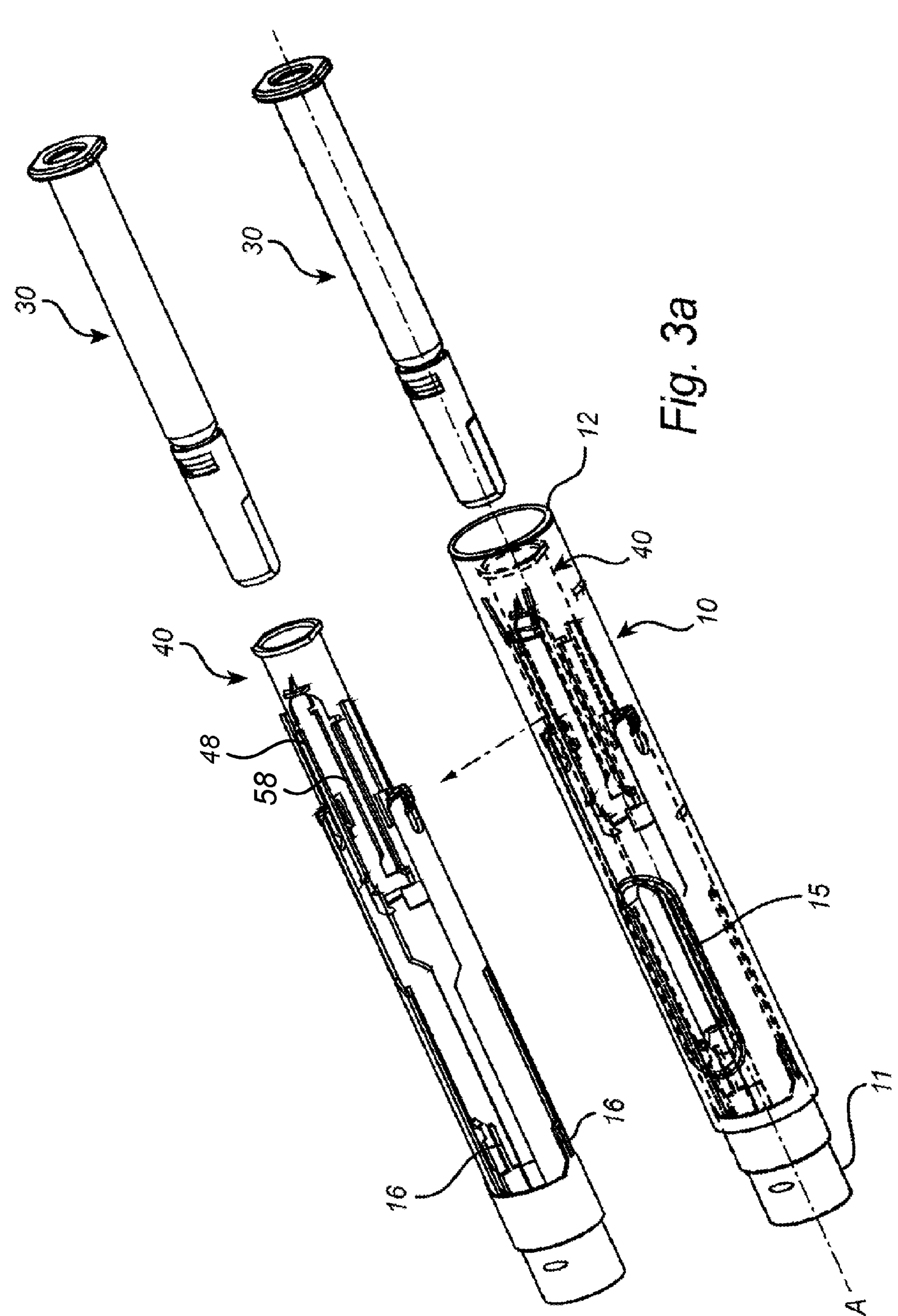
FIGS. 3*a*, 3*b* and 3*c* illustrate exploded views of the autoinjector device at different steps during the assembly of the autoinjector device.
Figure 3B:
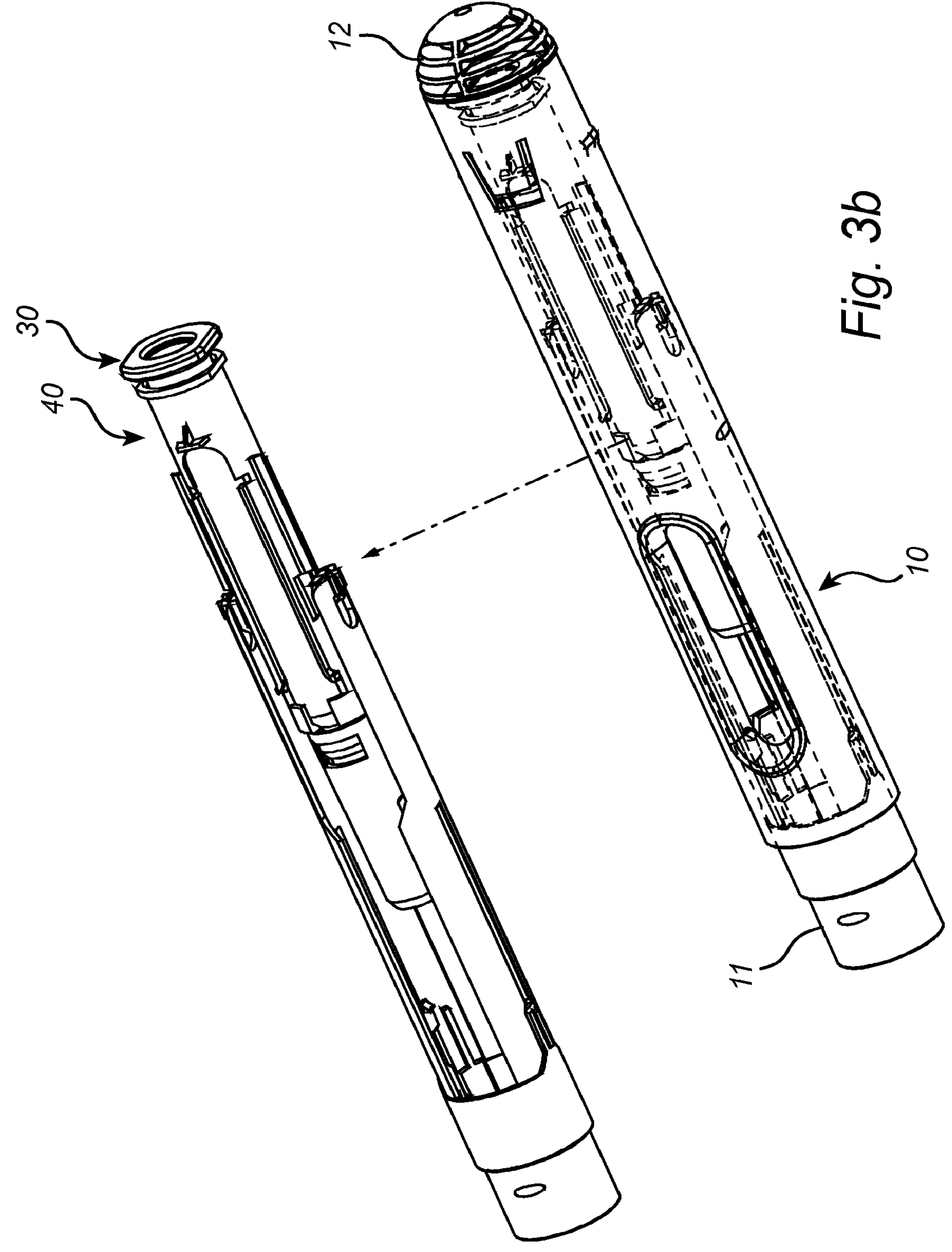
Figure 3C:
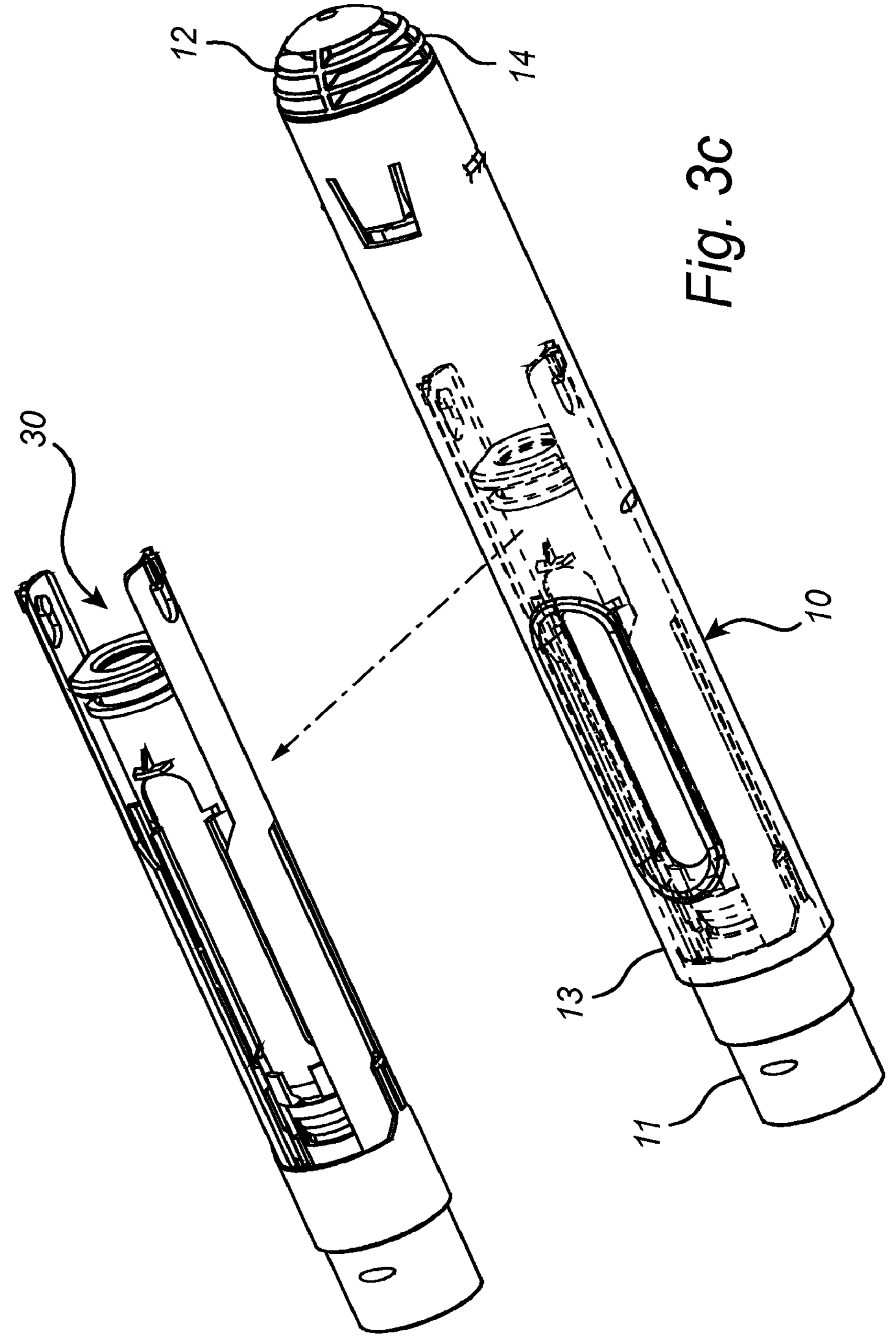

In FIGS. 3*a* to 3*c*, selected components of an autoinjector device 10 according to the invention are illustrated. The autoinjector device 10, elongated along a longitudinal axis A, is intended for self-administration of drugs and has a proximal end 11 and an opposing distal end 12.

The autoinjector device comprises an autoinjector housing divided into a proximal housing section 13 and distal housing section 14 in order to make the space defined inside the housing accessible for assembly of the different components of the autoinjector.

The autoinjector housing has the shape of a tube. The autoinjector housing is intended to house a pre-filled syringe 30 within a syringe holder 40. A drive mechanism (not shown) is also arranged within the housing. The drive mechanism is arranged to apply a proximally directed drive force to a movable plunger in the syringe in order to expel the drug through a needle (not shown).

The drive mechanism is not illustrated in detail in the drawings but different types of drive mechanisms are available. The drive mechanism may comprise a pre-tensioned spring which upon activation applies a pre-determined pressure via plunger rod (not shown) to the movable plunger arranged in a distal end of the syringe.

The autoinjector is intended for use in combination with a standard pre-filled syringe 30. The syringe 30, assembled in the syringe holder 40 illustrated in perspective in FIG. 2, has a substantially circular cross section having an outer diameter. The syringe is normally made of glass in order to ensure a reliable and hygenic storing of the drug in the syringe 30. At a proximal end of the syringe 30, the outer diameter is reduced and shaped like a neck 32 at which a needle (not shown) and needle shield 34 are attached before delivery of the syringe. In order to ensure that the needle remains sterilized before use, the needle is protected by the needle shield 34 having a substantially circular cross section and having an outer diameter which is larger than the outer diameter of the elongated syringe. The tubular needle shield 34 may be a so-called Rigid Needle Shield (RNS). Further, the tubular needle shield 34 encloses the needle and is removably fastened to the syringe 30 at the neck 32. The distal end of the tube-shaped syringe 30 is arranged with a radially extending flange 35. The syringe 30 furthermore comprises a movable plunger arranged in the distal end of the syringe 30 to seal the syringe 30 and ensure that the pre-filled drug of the syringe remains in the syringe 30. The movable plunger is preferably made of a rubber material in order to achieve a seal between the inner periphery of the syringe 30 and the plunger.

The syringe 30 is secured in the autoinjector housing by a syringe holder 40 that is described in more detail below. The syringe holder 40 is arranged in the proximal housing section in order to support and maintain the syringe 30 in a pre-determined position in relation to the syringe holder and the autoinjector housing. During assembly of the autoinjector, the syringe 30 is first inserted in the syringe holder 40, which is then moved in the proximal direction of the autoinjector device 10 to a forward position where the syringe holder 40 is secured in the proximal housing section. The movement of the syringe holder in the proximal housing section is facilitated by guiding means 41 consisting of corresponding longitudinal protrusions 42 along the outer periphery of the syringe holder 40 and longitudinal recesses along the inner periphery of the proximal housing section. Furthermore corresponding snap-fitting fastening means 43 are arranged on the syringe holder 40 and the proximal housing section in order to permanently secure the syringe holder in the desired proximal position within the proximal housing section.

Figure 1:
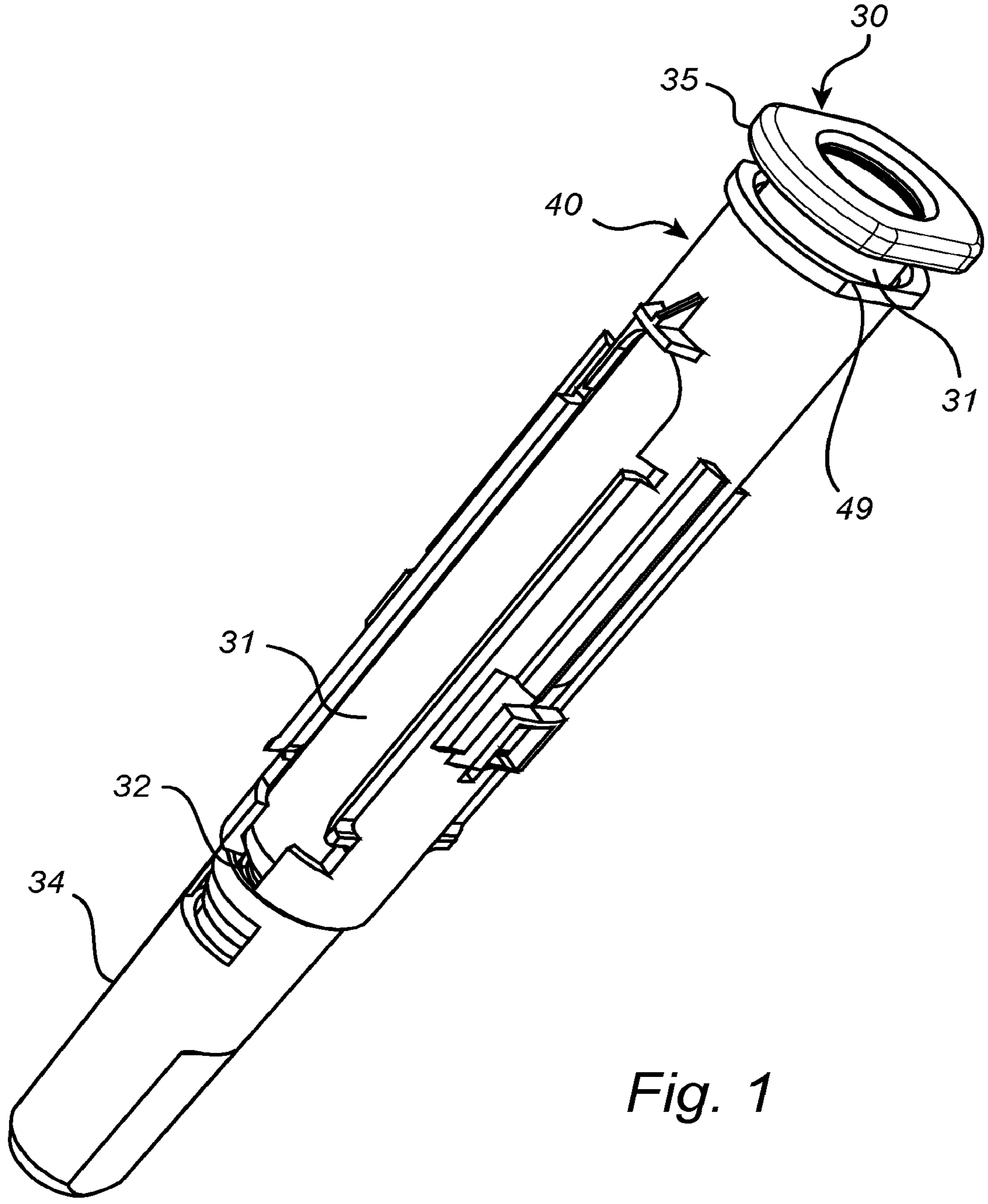
FIG. 1 illustrates a perspective view of a syringe assembled in a syringe holder.
Figure 2:
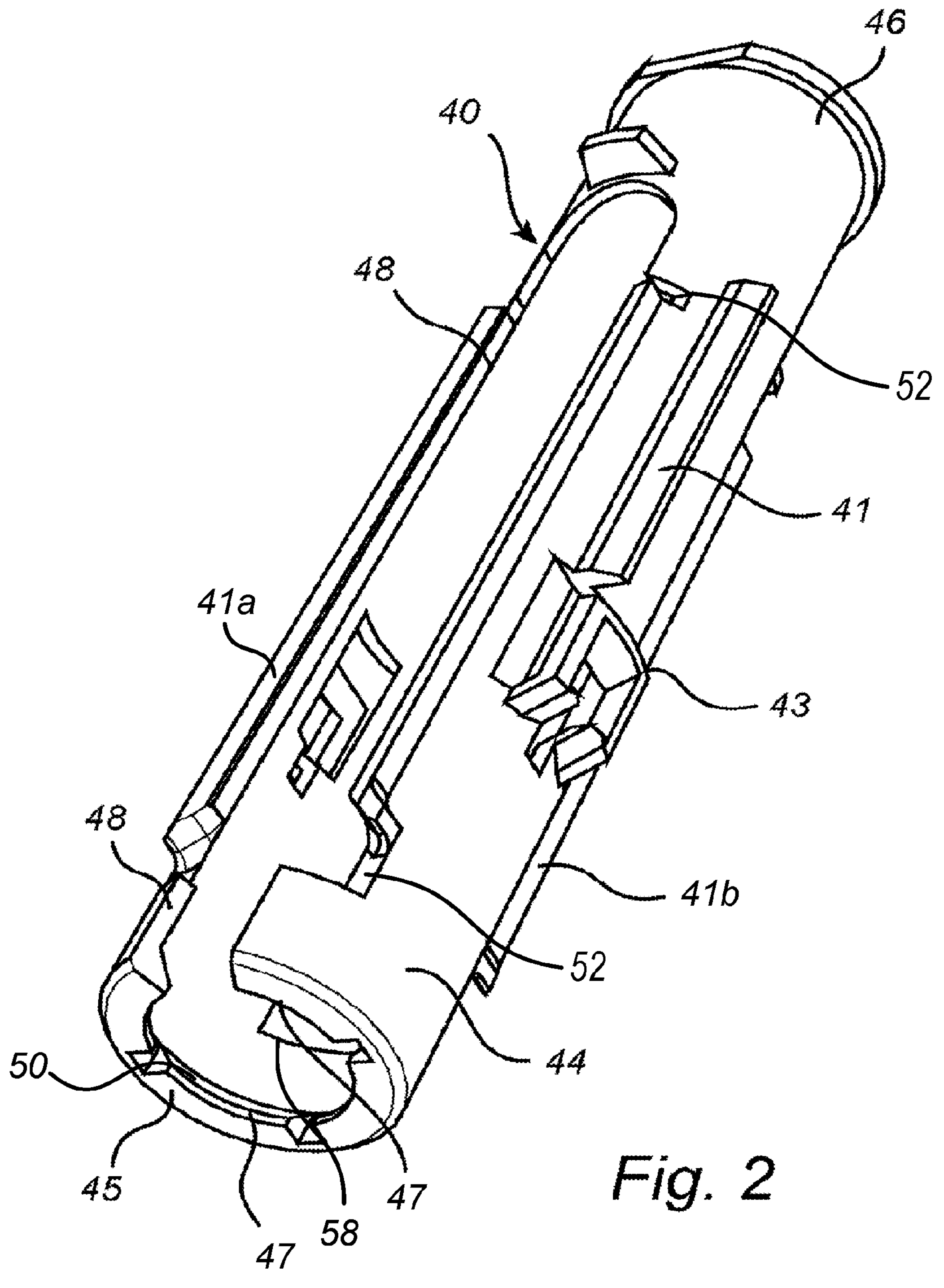
FIG. 2 illustrates a perspective view of a syringe holder.

The syringe holder 40 provides a reliable and effective support for the fragile syringe 30 and reduces the risk of damage to the syringe 30. One embodiment of the syringe holder 40 is illustrated in FIG. 2 in a perspective view, where it is separated from the other components of the autoinjector device. The syringe holder 40 has a tubularly shaped holder wall 44 with a proximal end 45 and a distal end 46. The proximal end 45 of the syringe holder is open but provided with a proximal supporting collar 47 arranged around the inner periphery of said syringe holder wall in order to support said syringe neck 32 in the proximal longitudinal direction. Further, the proximal supporting collar 47 has a inner diameter which is lesser than the outer diameter of the elongated syringe and thus also lesser than the outer diameter of the tubular needle shield. A slot 48 extends from said open proximal end in the distal direction resulting in a C-shaped cross sectional shape of the syringe holder wall in the proximal end. The C-shaped holder wall in the proximal end 45 is able to flex radially outward which is essential in order to fit the syringe 30 in the syringe holder 40 since the tubular needle shield 34 has an outer diameter exceeding the inner diameter of the opening in the proximal supporting collar 47. This means that the syringe 30 may be fitted in the syringe holder 40 from the distal end 46 of the syringe holder. The syringe 30 is then moved in the proximal direction within the syringe holder 40. When the tubular needle covering shield 34 reaches the proximal supporting collar 47, the C-shaped holder wall will flex radially outward and thereby make it possible to move the syringe 30 further until the neck 32 of the syringe 30 is in contact with the collar 47, i.e the desired position of the syringe 30 within the syringe holder 40. In this position the needle shield 34 has completely passed the supporting collar 47, allowing the C-shaped holder wall to flex back, radially inward, behind the needle shield, such that the collar supports the syringe at the neck 32.

The collar 47 can include a distally-facing contoured surface 50 configured to accommodate a distal portion of the neck 32 of the syringe 30.

The syringe holder 40 furthermore comprises a distal supporting collar 49 arranged around the outer periphery of said syringe holder wall 44 and has a longitudinal length between the proximal supporting collar 47 and a distal supporting collar 49 that corresponds to the length of the syringe 30 so that the distal supporting collar 49 of said syringe holder wall, when the syringe 30 is fitted in the desired position within the syringe holder 40, is in contact with the proximal side of the radially extending flange 35 of the syringe 30 and provides further support for the fragile syringe 30 within the syringe holder 40 at the same time as the proximal supporting collar 47 supports the neck 32 of said syringe 30. Thereby the risk of damage to the syringe 30 is reduced significantly. The syringe holder 40 furthermore comprises guiding means that facilitates its movement in the longitudinal direction of the autoinjector device and locking means for securing the syringe holder in the proximal housing section before assembly of the syringe in the syringe holder 40.

The proximal housing section is furthermore provided with a window 15, or opening, corresponding to the slot 48 in the syringe holder 40 when the syringe holder 40 is fitted in the intended position in the proximal housing section in order to make the syringe 30, and the drug in the syringe, visible from the outside of the autoinjector housing and possible for the patient to verify that the autoinjector device is correctly assembled and ready for use.

The syringe holder 40 can define a first cut-out 48 along the syringe holder 40 proximal to the distal supporting collar 49 and a second cut-out 58, the first cut-out 48 being opposite the second cut-out 58. The syringe holder 40 can include a first projection 41*a* that extends along an edge of the first cut-out 48 and a second projection 41*b* that extends along an edge of the second cut-out 58. The syringe holder wall 44 can define a recess 52 adjacent the first cut-out 48.

Three different assembly steps of the autoinjector device are schematically illustrated in FIGS. 3*a*-3*c*. In FIG. 3*a*, the proximal housing section and the syringe holder 40 are illustrated without the syringe 30 fitted in the syringe holder 40. The syringe holder 40 is movably arranged in the proximal housing section between a distal position and a proximal position. Prior to fitting the syringe in the syringe holder the syringe holder is arranged in the distal position ready for assembly.

The assembly of the autoinjector device 10 is initiated by fitting the syringe 30 in the syringe holder 40 by inserting the proximal end of the syringe in the distal end of the syringe holder 40 and pushing the syringe in the proximal direction until the neck 32 of the syringe 30 is in contact with the collar 47 in the proximal end of the syringe holder 40, illustrated in FIG. 3*b*. The syringe 30 and the syringe holder 40 are then moved simultaneously in the proximal direction to the proximal position in the proximal housing section. In the proximal position, the outer periphery of the proximal end of the syringe holder 40 will be surrounded by support surfaces 16 on the inside surface of the proximal housing section. The cross sectional shape of the support surfaces correspond to the outer periphery of the syringe holder in order to provided a rigid support and prevent the C-shaped wall of the proximal end from flexing radially outwards in order to secure the syringe 30 in the syringe holder 40 and the autoinjector device 10, illustrated in FIG. 3*c*. Finally, the autoinjector housing is closed around the syringe 30 by fitting the distal housing section to the proximal housing section.

The assembly method of the present invention accordingly comprises the steps:

a). Inserting the proximal end of the syringe 30 in the distal end of the syringe holder 40;

b). Moving the syringe 30 towards the proximal end of the syringe holder until the neck 32 of the syringe 30 is in contact with the proximal supporting collar 47 and the radially extending flange 35 of the syringe 30 in contact with the distal supporting collar 49 of the syringe holder 40;

c). Moving the syringe holder 40 and the syringe 30 simultaneously towards the proximal end of the autoinjector device 10.

The different embodiments described above could be combined in different ways and modified further without departing from the scope of the invention that is defined by the claims.

The invention claimed is:

1. A syringe carrier comprising:

an elongate body comprising a collar at a distal end of the elongate body, the collar configured to allow a syringe to be slid proximally through the collar, the elongate body configured to receive a barrel of the syringe, the elongate body defining a first cut-out along the elongate body proximal to the collar and a second cut-out along the elongate body proximal to the collar, the first cut-out being opposite the second cut-out, the elongate body comprising a first projection that extends along an edge of the first cut-out and a second projection that extends along an edge of the second cut-out, the first and second cut-outs arranged to provide visual access to the barrel of the syringe when the syringe is disposed in the recess of the syringe carrier, wherein a proximal end region of the elongate body comprises at least one inwardly extending projection configured to be disposed in a gap formed between a rigid needle shield of the syringe and the barrel of the syringe and configured to contact the syringe to restrict proximal axial movement of the syringe relative to the syringe carrier when the syringe is disposed in the syringe carrier.

2. The syringe carrier of claim 1, wherein the first cut-out extends to a proximal end of the elongate body.

3. The syringe carrier of claim 1, wherein a proximal surface of the elongate body is c-shaped.

4. The syringe carrier of claim 3, wherein the first cut-out extends from a proximal end of the elongate body approximately to the collar.

5. The syringe carrier of claim 1, wherein the rigid needle shield has an outer diameter substantially equal to an outer diameter of the barrel of the syringe.

6. The syringe carrier of claim 1, wherein the first and second cut-outs are windows.

7. The syringe carrier of claim 1, wherein the proximal end region of the elongate body is c-shaped and is configured to deflect radially outwardly as the syringe is slid proximally through the collar and the rigid needle shield contacts the at least one inwardly extending projection, and the c-shaped proximal end region of the elongate body is configured to rebound radially inwardly when the rigid needle shield moves proximally beyond the at least one inwardly extending projection.

8. The syringe carrier of claim 7, wherein the at least one inwardly extending projection is configured to contact a proximal end of the barrel of the syringe when the c-shaped proximal end region of the elongate body has rebounded radially inwardly.

9. The syringe carrier of claim 8, wherein the contact of the at least one inwardly extending projection and the proximal end of the barrel of the syringe restricts the proximal axial movement of the syringe relative to the syringe carrier.

10. The syringe carrier of claim 1, wherein the at least one inwardly extending projection has a distally-facing contoured surface configured to accommodate a distal portion of the neck of the syringe.

11. The syringe carrier of claim 10, wherein the at least one inwardly extending projection has a proximally-facing planar surface configured to abut a distal end of the rigid needle shield of the syringe.

12. The syringe carrier of claim 1, wherein the rigid needle shield has an outer diameter greater than an inner diameter defined by the at least one inwardly extending projection when the proximal end region of the elongate body is in an undeflected position.

13. The syringe carrier of claim 1, wherein the syringe carrier is configured so that a finger flange of the syringe is spaced distally from the collar of the syringe carrier when the syringe is inserted in the syringe carrier and the at least one inwardly extending projection is disposed in the gap formed between the rigid needle shield and the barrel of the syringe.

14. The syringe carrier of claim 1, wherein a proximal surface of the elongate body abuts the rigid needle shield.

15. The syringe carrier of claim 1, wherein the first cut-out is a slot formed in a portion of the elongate body proximal to the collar, and the portion of the elongate body forming the slot is adapted to flex radially inward over the barrel of the syringe when the proximal end region of the syringe carrier rebounds radially inward as the syringe is inserted into the syringe carrier.

16. The syringe carrier of claim 1, wherein the elongate body defines a recess adjacent the first cut-out.

17. A syringe carrier comprising:

an elongate body having a c-shaped proximal surface and comprising a collar at a distal end of the elongate body, the collar configured to allow a syringe to be slid proximally through the collar, the elongate body configured to receive a barrel of the syringe, the elongate body defining a first cut-out along the elongate body proximal to the collar and a second cut-out along the elongate body proximal to the collar, the first cut-out being opposite the second cut-out, the first cut-out extending distally from a proximal end of the elongate body, the elongate body comprising a first projection that extends along an edge of the first cut-out and a second projection that extends along an edge of the second cut-out, the first and second cut-outs arranged to provide visual access to the barrel of the syringe when the syringe is disposed in the syringe carrier, wherein a proximal end region of the elongate body comprises at least one inwardly extending projection configured to be disposed in a gap formed between a rigid needle shield of the syringe and the barrel of the syringe, and wherein a proximal end region of the elongate body is configured to deflect radially outwardly as the syringe is slid proximally through the collar and the rigid needle shield contacts the at least one inwardly extending projection, and the proximal end region of the elongate body is configured to rebound radially inwardly when the rigid needle shield moves proximally beyond the at least one inwardly extending projection, wherein the at least one inwardly extending projection is configured to contact a proximal end of the barrel of the syringe when the proximal end region of the elongate body has rebounded radially to restrict proximal axial movement of the syringe relative to the syringe carrier, and wherein the syringe carrier is configured so that a finger flange of the syringe is spaced distally from the collar of the syringe carrier when the at least one inwardly extending projection is disposed in the gap between the rigid needle shield of the syringe and the barrel of the syringe.

18. An assembly comprising:

a syringe comprising a barrel, a neck extending proximally from the barrel, a finger flange extending from a distal end portion of the barrel, a needle extending proximally from the neck, and a rigid needle shield covering the needle; and a syringe carrier comprising an elongate body comprising a collar at a distal end of the elongate body, the collar configured to allow the syringe to be slid proximally through the collar, the elongate body configured to receive the barrel of the syringe, the elongate body defining a first cut-out along the elongate body proximal to the collar and a second cut-out along the elongate body proximal to the collar, the first cut-out being opposite the second cut-out, the elongate body comprising a first projection that extends along an edge of the first cut-out and a second projection that extends along an edge of the second cut-out, the first and second cut-outs arranged to provide visual access to the barrel of the syringe when the syringe is disposed in the recess of the syringe carrier, wherein a proximal end region of the elongate body comprises at least one inwardly extending projection configured to be disposed in a gap formed between the rigid needle shield of the syringe and the barrel of the syringe and to contact the syringe to restrict proximal axial movement of the syringe relative to the syringe carrier when the syringe is disposed in the recess of the syringe carrier.

19. The assembly of claim 18, wherein the syringe contains medicament.

20. An autoinjector comprising:

a housing; and a syringe carrier configured to be disposed in the housing, the syringe carrier comprising an elongate body comprising a collar at a distal end of the elongate body, the collar configured to allow a syringe to be slid proximally through the collar, the elongate body configured to receive a barrel of the syringe, the elongate body defining a first cut-out along the elongate body proximal to the collar and a second cut-out along the elongate body proximal to the collar, the first cut-out being opposite the second cut-out, the elongate body comprising a first projection that extends along an edge of the first cut-out and a second projection that extends along an edge of the second cut-out, the first and second cut-outs arranged to provide visual access to the barrel of the syringe when the syringe is disposed in the recess of the syringe carrier, wherein a proximal end region of the elongate body comprises at least one inwardly extending projection configured to be disposed in a gap formed between a rigid needle shield of the syringe and the barrel of the syringe and to contact the syringe to restrict proximal axial movement of the syringe relative to the syringe carrier when the syringe is disposed in the recess of the syringe carrier and the syringe carrier is disposed in the housing of the autoinjector.

* * * * *